US00PP22074P2

(12) United States Plant Patent
Klemm et al.

(10) Patent No.: US PP22,074 P2
(45) Date of Patent: Aug. 9, 2011

(54) ***OSTEOSPERMUM* PLANT NAMED 'KLEOE09164'**

(50) Latin Name: ***Osteospermum ecklonis* Norl.**
Varietal Denomination: KLEOE09164

(75) Inventors: Nils Klemm, Stuttgart (DE); Andrea Dohm, Pforzheim (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/798,140

(22) Filed: Mar. 30, 2010

(51) Int. Cl.
*A01H 5/00* (2006.01)

(52) U.S. Cl. ..... Plt./360

(58) Field of Classification Search ..... Plt./360
See application file for complete search history.

*Primary Examiner* — Susan McCormick Ewoldt
(74) *Attorney, Agent, or Firm* — Jondle & Associates, P.C.

(57) ABSTRACT

An *Osteospermum* variety named 'KLEOE09164' particularly distinguished by a very early flowering time, a very compact growth habit, and excellent branching, is disclosed.

1 Drawing Sheet

Genus and species: *Osteospermum ecklonis* Norl.
Variety denomination: 'KLEOE09164'.

BACKGROUND OF THE NEW PLANT

The present invention comprises a new and distinct variety of *Osteospermum*, botanically known as *Osteospermum ecklonis* Norl., and hereinafter referred to by the variety name 'KLEOE09164'. The new variety originated from an open pollination made in August 2005 in Stuttgart, Germany. The female parent was a proprietary *Osteospermum* plant named 'KLEO03106' (unpatented), and the male parent was an unknown *Osteospermum* plant (unpatented).

The new variety was first propagated via vegetative cuttings in May 2006 in Stuttgart, Germany and has been asexually reproduced repeatedly by vegetative cuttings in Stuttgart, Germany for more than 15 generations. The present invention has been found to retain its distinctive characteristics through successive asexual propagations via vegetative cuttings.

Plant Breeder's Rights for this variety have not been applied for. 'KLEOE09164' has not been made publicly available or sold more than one year prior to the filing date of this application.

SUMMARY OF THE INVENTION

The following are the most outstanding and distinguishing characteristics of the new variety when grown under normal horticultural practices in Stuttgart, Germany.

1. A very early flowering time;
2. A very compact growth habit; and
3. Excellent branching.

DESCRIPTION OF THE PHOTOGRAPH

This new *Osteospermum* plant is illustrated by the accompanying photograph which shows a close-up of a flower of the plant. The colors shown are as true as can be reasonably obtained by conventional photographic procedures. The photograph was taken in Summer 2009 of a 7-month-old plant in the field in Stuttgart, Germany, under conditions which approximate those generally used in commercial practice.

DESCRIPTION OF THE NEW VARIETY

The following detailed descriptions set forth the distinctive characteristics of 'KLEOE09164'. The data which define these characteristics were collected from asexual reproductions carried out in Stuttgart, Germany. The plant history was taken in Summer 2009 on 7-month-old plants which were potted at 4 weeks in 12 centimeter containers and then planted in the ground in calendar week 20. The plants were pinched once at 6 weeks. Color readings were taken under natural light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:
- *Family.*—Asteraceae.
- *Botanical name.*—*Osteospermum ecklonis* Norl.
- *Common name.*—African daisy.

Parentage:
- *Female parent.*—A proprietary *Osteospermum* plant named 'KLEO03106' (unpatented).
- *Male parent.*—An unknown *Osteospermum* plant (unpatented).

Plant:
- *Form and habit.*—Semi-upright (V-shape).
- *Growth habit.*—Compact.
- *Branching habit.*—Excellent branching.
- *Height (from top of soil, including inflorescence).*—40.0 cm to 45.0 cm.
- *Width (including inflorescences).*—50.0 cm.
- *Propagation.*—Vegetative cuttings.
- *Time to produce a finished flowering plant.*—15 weeks from sticking.
- *Time to initiate and develop roots.*—3 weeks.
- *Root description.*—Freely rooting.

Leaves:
- *Arrangement.*—Alternate.
- *Shape.*—Obovate.
- *Apex.*—Acute.
- *Base.*—Acute.
- *Margin.*—Serrate.
- *Color.*—Immature leaf: Upper surface: RHS 137C. Lower surface: RHS 137D. Mature leaf: Upper surface: RHS N137C. Lower surface: RHS 137C.

*Length.*—5.0 cm to 5.7 cm.
*Width.*—2.0 cm.
*Texture.*—Glabrous on the upper surface.
*Appearance.*—Leathery on the upper surface.
*Petioles.*—Absent.
*Venation pattern.*—No venation.

Stems:
*Total number of branches.*—Approximately 10 to 12.
*Length.*—40.0 cm to 45.0 cm.
*Diameter.*—0.5 cm.
*Internode length.*—0.5 cm to 1.0 cm.
*Color.*—RHS 138B.
*Texture.*—Glabrous.
*Appearance.*—Leathery.
*Anthocyanin.*—Absent.

Inflorescence buds:
*Shape.*—Obovate.
*Length.*—2.0 cm.
*Diameter.*—1.0 cm.
*Color* (*at tight bud just before the ray florets unfold*).—RHS 143B.

Inflorescence:
*Type.*—Composite.
*Blooming habit.*—Plants flower continuously from early Spring to Fall.
*Quantity of inflorescences per plant.*—Approximately 150.
*Lastingness of the inflorescences on the plant.*—10 days.
*Fragrance.*—Absent.
*Inflorescence diameter.*—6.0 cm to 7.0 cm.
*Inflorescence depth.*—Approximately 1.0 cm.
*Disc diameter.*—1.0 cm.

Disc floret:
*Quantity per inflorescence.*—Approximately 50.
*Shape.*—Tubular, radially symmetrical.
*Tube color.*—Closed: RHS 2D and RHS 86B. Mature: RHS 2D and RHS 94B.
*Length.*—Approximately 0.6 cm.
*Diameter* (*at apex*).—0.3 cm.
*Apex.*—Acuminate.
*Apex color.*—RHS 94B.
*Base.*—Obtuse.
*Base color.*—RHS 2D.
*Margin.*—Entire.

Ray floret:
*Quantity per inflorescence.*—15 to 20.
*Shape.*—Lanceolate.
*Color.*—Upper surface: RHS 155C. Lower surface: RHS 77D and RHS 12B and RHS 155C (stripes).
*Length.*—3.0 cm.
*Width.*—1.0 cm.
*Apex.*—Obtuse.
*Base.*—Acute.
*Margin.*—Entire.
*Texture.*—Smooth.
*Peduncle.*—Length: 12.0 cm. Diameter: 0.2 cm. Texture: Rough. Color: RHS 143C.

Phyllaries:
*Arrangement.*—Single.
*Observed quantity per plant.*—15 to 20.
*Shape.*—Lanceolate.
*Color* (*both upper and lower surfaces*).—RHS 143C.
*Length.*—1.0 cm.
*Width.*—0.2 cm.
*Apex.*—Acute.
*Base.*—Obtuse.
*Margin.*—Entire.
*Texture.*—Rough.

Reproductive organs:
*Androecium.*—Location: In the disc floret. Stamens: Quantity: 50. Shape: Tubular. Color: RHS 95A. Filament length: 0.5 cm. Filament diameter: 0.1 cm. Anther: Shape: Longitudinal. Color: RHS N186A. Length: 0.3 cm. Diameter: 0.1 cm. Pollen: Color: RHS 162A. Amount: Moderate.
*Gynoecium.*—Location: On the base of the ray floret; gynoecium in the disc floret is not functional. Pistils: Number: 15 to 20. Length: 0.3 cm. Diameter: 0.05 cm. Stigma: Color: RHS 92B. Shape: Ovate. Length: 0.2 cm. Diameter: 0.001 cm. Style: Color: RHS 92B. Length: 0.3 cm. Diameter: 0.001 cm.

Fruit and seed set: Dark brown, torpedo-shaped seeds; moderate seed set observed.

Disease and insect resistance: No particular disease or insect resistance observed.

COMPARISON WITH PARENTAL AND COMMERCIAL VARIETIES

'KLEOE09164' differs from the female parent, the proprietary *Osteospermum* plant named 'KLEO03106' (unpatented), in that 'KLEOE09164' has an earlier flowering time and better branching than 'KLEO03106'. In addition, 'KLEOE09164' has a more compact growth habit than 'KLEO03106'.

'KLEOE09164' differs from the commercial variety 'KLEOE06123' (unpatented) in that 'KLEOE09164' has an earlier flowering time and better branching than 'KLEOE06123'. In addition, 'KLEOE09164' has a more compact growth habit than 'KLEOE06123'. Further, 'KLEOE09164' has lower petals that are pink-grey in color, whereas 'KLEOE06123' has lower petals that are blue-grey in color.

We claim:

1. A new and distinct variety of *Osteospermum* plant named 'KLEOE09164' as shown and described herein.

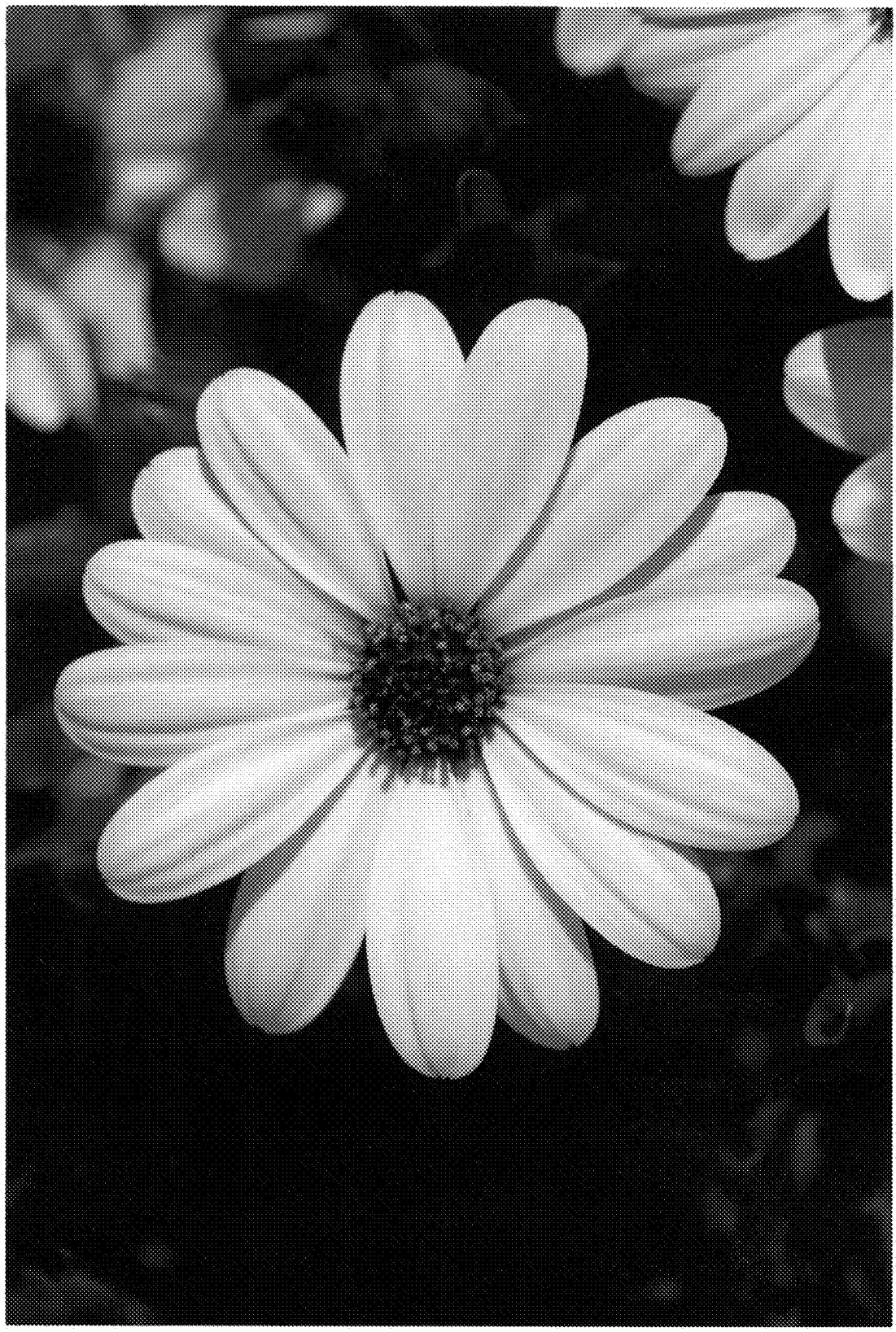

* * * * *